United States Patent [19]

Kaufman

[11] 4,321,752

[45] Mar. 30, 1982

[54] METHOD AND APPARATUS FOR MEASURING BODY FAT

[76] Inventor: Richard C. Kaufman, Kingswood Village Marina, 4145 A Via Marina-#108, Marina Del Rey, Calif. 90291

[21] Appl. No.: 114,104

[22] Filed: Jan. 16, 1980

[51] Int. Cl.³ .............................................. G01B 5/18
[52] U.S. Cl. ................................. 33/169 B; 33/174 D
[58] Field of Search ............. 33/169 B, 174 D, 169 R, 33/154 C, 170

[56] References Cited

U.S. PATENT DOCUMENTS 1,248,340  11/1917  Kinney ............................. 33/169 B Primary Examiner—Willis Little
Attorney, Agent, or Firm—Harvey B. Jacobson

[57] ABSTRACT

An apparatus comprising an elongated scale slidably disposed through a planar base is used to provide a direct measurement of height of fat in subcutaneous tissue in the abdominal area. The scale is inserted into the orifice about a subject's umbilicus until it contacts the umbilicus. The scale is kept perpendicular to the umbilicus while the planar base is slid down over the scale until the bottom surface of the base makes light contact on the surface on the stomach. A reading of the thickness of the fat and subcutaneous tissue can then be taken from the scale.

6 Claims, 4 Drawing Figures

METHOD AND APPARATUS FOR MEASURING BODY FAT

BACKGROUND OF THE INVENTION

1. Field of the Invention

This invention relates to a method and apparatus for assessing quantitively the fat content of a human body.

2. Discussion of Related Art

Obesity is a probelm of considerable concern among both doctors and the patients. Obesity cannot only be a severe health hazard, but also makes the obese person feel unattractive causing social disfunctions. Accordingly, the ability to diagnose the existence of and determine the degree of obesity in human patients is desirable.

Obesity can be defined as excess fat accumulation. Most people associate body weight with body fatness and thus associate being overweight with having an excess amount of body fat. It is an error to associate fatness with being overweight and thinness with being underweight. It is known that athletes are often overweight and at the same time under fat, while sedentary people are sometimes underweight and over fat.

Thus it can be seen that the use of height and weight charts, one of the more common presently used methods to attempt to determine excess body fat, can be highly inaccurate and misleading. A practical measuring device is required to measure body fat.

One presently accepted method of determining actual body fat comprises skin fold measurements. Calipers, such as those shown in U.S. Pat. No. 3,008,239, issued Nov. 14, 1961, to Lange, are used to measure the thickness of a fold of skin in various areas of the body. Regression equations have been developed which can translate this measurement into a logarithmic value which then can be translated into a percent designation of body weight which comprises body fat.

The skin fold technique, while accurate, requires the use of expensive calipers which require technical skill in their use. Further, such calipers are difficult to use in the abdominal area which area provides a higher degree of correlation with body fat than the more commonly used arm skin fold measurement. Therefore, a need has developed for a simple device and procedure for measuring skin thickness in the abdomen.

One tool designed for measuring the thickness of fat is shown in U.S. Pat. No. 3,979,835, issued Sept. 14, 1976, to Sumption, et al. The Sumpton et al device, however, is designed for measuring thickness of fat in a carcass by inserting the measuring tool into the fat itself and thus requires puncturing the skin. U.S. Pat. No. 4,078,313, issued Mar. 14, 1978, to Hennessy, shows a measuring device for measuring animal fat by insertion of a probe directly into the fat. U.S. Pat. No. 2,763,935, issued Sept. 25, 1956, to Whaley et al, shows yet another device for measuring the depth of animal fat which device requires actual penetration of the fat being measured.

Of course, depth measuring gauges per se are also known. For instance, U.S. Pat. No. 3,813,785, issued June 4, 1974, to Larsen, shows a veneer block for attachment to a standard measuring blade. U.S. Pat. No. 2,179,658, issued Nov. 14, 1939, to Gallagher, shows an electrician's guide having a scale with a transverse member slidably disposed on the scale. Other similar devices are shown in U.S. Pat. Nos. 1,009,605, issued Nov. 21, 1911, to Walker, 1,248,340, issued Nov. 27, 1917, to Kinney and 2,373,338, issued Apr. 10, 1945, to Rakauskas. Since each of these devices comprises a slidable keeper with a small surface contact area, if the devices are used for measuring a hole with an uneven top surface, different height readings will be indicated depending on what point of the top surface is contacted by the slidable keeper. Further, the small rectangular contact surface will only keep the device precisely perpendicular in one plane. This also reduces the accuracy of any readings obtained.

SUMMARY OF THE INVENTION

One object of the present invention is to provide an apparatus and method for measuring the thickness of abdominal skin in a human subject without the necessity of piercing or puncturing the skin itself.

A further object of the present invention is to provide a method and apparatus for measuring body fat which can give a direct reading of percent body fat.

A yet still further object of the present invention is to provide a method and apparatus for measuring body fat wherein the apparatus is inexpensive and can be used easily and accurately by an unskilled person.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
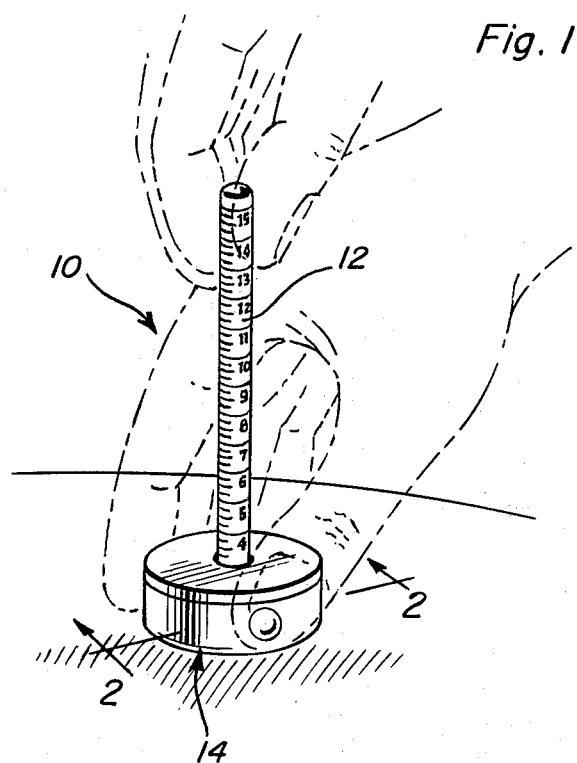
FIG. 1 is a perspective view of the apparatus of the present invention shown in position for measuring body fat.
Figure 2:
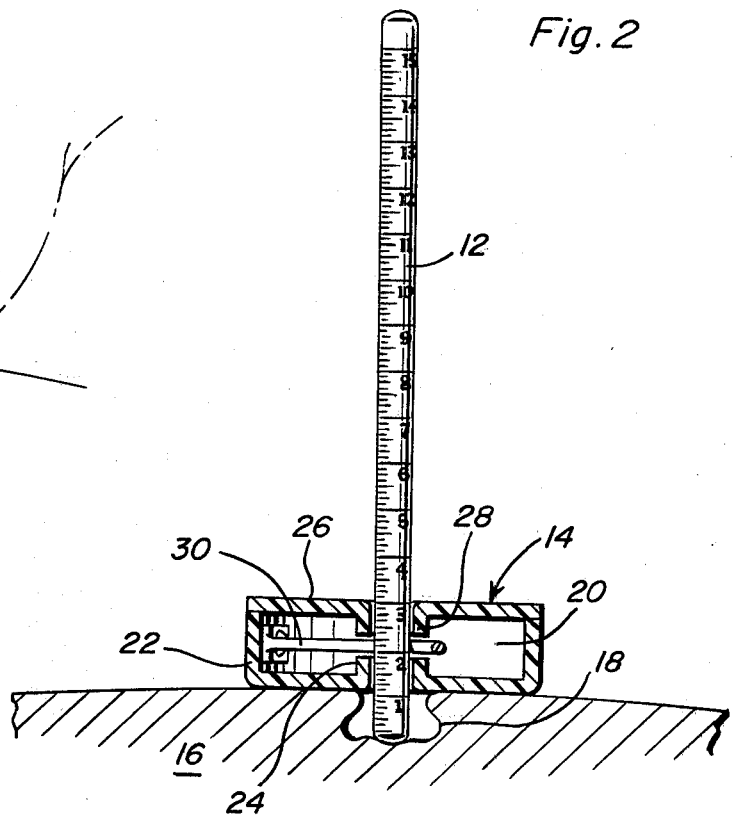
FIG. 2 is an elevational sectional view taken substantially along a plane passing through section line 2—2 of FIG. 1.
Figure 3:
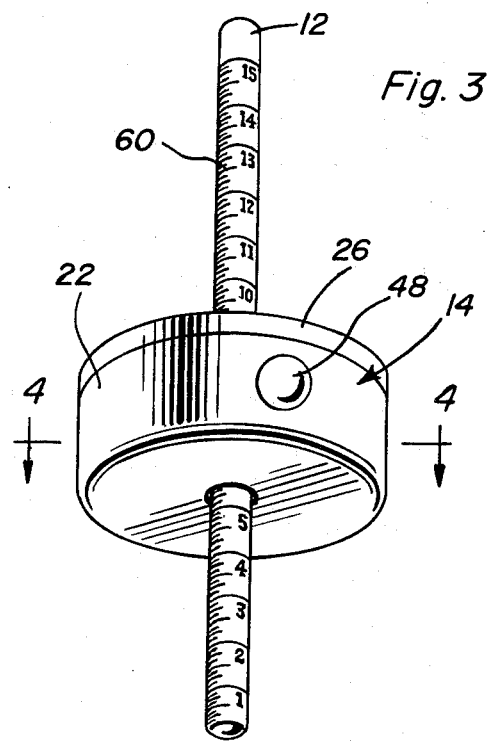
FIG. 3 is a perspective view of the apparatus of the present invention.
Figure 4:
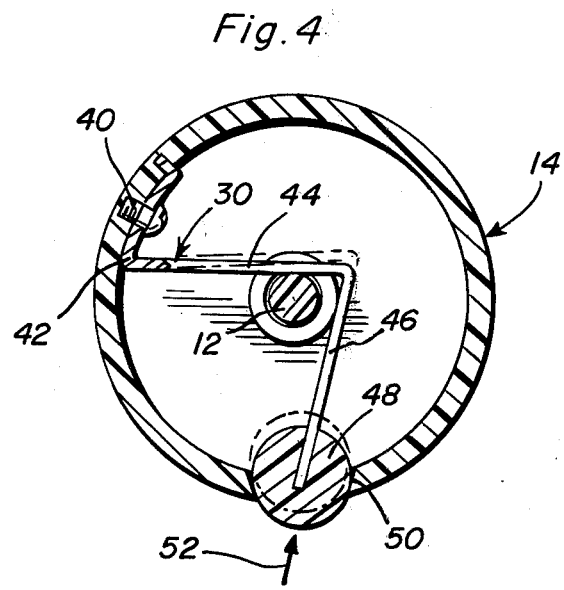
FIG. 4 is a top plan sectional view taken substantially along a plane passing through section line 4—4 of FIG. 3.

Now with reference to the drawings, the method of and apparatus for measuring body fat will be described in detail. The apparatus is generally labelled with the reference numeral 10 and comprises an elongated cylindrical shaft 12 slidably disposed in a base 14. The base 14 rests on the abdomen 16 in the area of the subject's umbilicus 18. In order not to cause any compression of the fat covering the stomach on which it rests, the base 14 is made from a plastic shell having hollow interior 20, thus reducing the weight of the base. The base 14 comprises a cup-shaped cylindrical lower portion 22 which has an inner upstanding annular flange 24 which surrounds and snugly receives the shaft 12. A disc shaped top 26 is disposed over the bottom portion and includes a depending annular flange 28 which is spaced vertically from annular flange 24 and also surrounds and snugly receives the shaft 12. Shaft 12 can slide vertically within the flanges 24 and 28. The lower portion 22 has a planar lower surface which rests on the abdomen itself.

Disposed within the hollow interior 20 of the base 14 is a spring steel lock clip 30 which is biased against shaft 12. Clip 30 is screwed into the lower portion 22 of the base 14 by use of screw 40. The clip is bent at 42 and has one leg 44 which is actually biased against the shaft 12. A second leg 46 extends past the shaft 12 and is attached to a ball 48 which protrudes through an opening 50 in the base 14. Accordingly, pressure can be applied radially inward on the ball 48 as depicted by arrow 52 in order to release tension from the shaft 12 to allow the shaft to move vertically within the base. In the locked position, the clip 30 exerts pressure on the shaft 12 and prevents it from moving up and down in the base.

The shaft 12 itself has an approximate diameter of 7 mm. and a nominal length of 15 cm. Inscribed along the entire length of the shaft is a scale 60 with divisions of 1 mm. The scale need not be in millimeters but only in a system capable of being read. The scale goes from 0 to 150 mm. The 0 millimeter and end of the shaft 12 is slightly blunted to a cone.

The skin fold method of body fat measurement comprises a double thickness measurement of subcutaneous skin and fat. Muscle and fascia are not measured. With a fatless reference point starting at a muscle level the height of fat and subcutaneous tissue can be measured directly. Instead of a double fold there would really be a single height measurement directly correlating with the percent of body fat. The umbilicus is a fatless puckered scar in the shape of small orifice surrounded by fat and subcutaneous tissue on the stomach muscles suitable for use as a reference point. With the device 10, the thickness of fat in the umbilical region can easily be measured and translated into a percent of body fat reading.

In operation, the subject whose body fat percentage is to be determined is instructed to lie in a supine position flat on their back on a hard straight surface. The umbilicus and stomach region of the subject are exposed. The base 12 is positioned on the device at the level of 150 mm. mark. The blunted end of the shaft 12 is gently inserted into the umbilical orifice surrounding the umbilicus unit it rest gently on the umbilicus. One hand holds the cylinder stationary and perpendicular to the surface of the stomach. The other hand depresses ball 48 to release shaft 12 and slides the base 14 down the cylinder shaft until the lower surface of the disc makes contact with the stomach's surface. Upon contact, the device 10 is removed from the umbilicus without moving the base relative to the shaft. The distance from the umbilicus to the top of the stomach surface is read on the scale and the scale value is translated into a percent body fat on appropriate obesity standard scale sheets. Data can be provided for the recommended and average percent of body fat for different age groups and sex. Such data is standardly available.

Because the scale on shaft 12 can be directly translated into a percent body fat reading, the scale could be constructed to read percent body fat, but this would require separate male and female devices. Depending upon the degree of accuracy required, there could be different shafts for different age groups of males and females. This is due to topographical differences in the relative distribution of fat between the sexes and between the ages of different sexes. Such could be taken into account by the use of a shaft having a square or triangular cross section so that the different values could be placed on different faces of the shaft.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An apparatus for measuring body fat, comprising: a base having a large planar lower contact surface and an elongated scale slidably disposed through said base in perpendicular relation to said contact surface, said base comprising a hollow housing, said housing having mounted therein a spring clip biased against said scale for holding said scale in a preset condition, said apparatus further including a knob mounted upon said spring clip and extending through said base and accessible outside of said base for disengaging said spring clip from said scale by depressing the accessible portion of said knob.

2. The apparatus as defined in claim 1 wherein said housing has a sleeve disposed centrally thereof through which said elongated scale is slidably disposed.

3. The apparatus as defined in claim 2 wherein said sleeve is formed in two annular portions, one of said annular portions being axially spaced from the other of said annular portions.

4. The apparatus as defined in claim 1 wherein said spring clip is formed with two angularly oriented legs, one of said legs being biased against said scale and the other of said legs extending substantially radially of said housing, said knob being mounted on said other of said legs.

5. The apparatus as defined in claim 4 wherein said scale is substantially cylindrical in shape.

6. The apparatus as defined in claim 4 wherein said scale has a plurality of sides.

* * * * *